US008235884B2

(12) United States Patent
Royalty et al.

(10) Patent No.: US 8,235,884 B2
(45) Date of Patent: Aug. 7, 2012

(54) CARDIAC TISSUE ENERGY DISPERSION DEVICE

(76) Inventors: John W Royalty, Crystal River, FL (US); Lawrence A Lynn, Columbus, OH (US)

( * ) Notice: Subject to any disclaimer, the term of this patent is extended or adjusted under 35 U.S.C. 154(b) by 811 days.

(21) Appl. No.: 11/648,914

(22) Filed: Jan. 3, 2007

(65) Prior Publication Data
US 2007/0238914 A1 Oct. 11, 2007

Related U.S. Application Data

(60) Provisional application No. 60/755,413, filed on Dec. 31, 2005, provisional application No. 60/755,414, filed on Dec. 31, 2005, provisional application No. 60/755,415, filed on Dec. 31, 2005, provisional application No. 60/755,416, filed on Dec. 31, 2005, provisional application No. 60/755,424, filed on Dec. 31, 2005.

(51) Int. Cl.
*A61B 1/04* (2006.01)
*A61N 1/00* (2006.01)
(52) U.S. Cl. .......................................... 600/16; 607/129
(58) Field of Classification Search ................. 607/129; 600/16
See application file for complete search history.

(56) References Cited

U.S. PATENT DOCUMENTS

| 5,498,228 | A  | * | 3/1996 | Royalty et al. ............... 600/16 |
| 6,567,699 | B2 | * | 5/2003 | Alferness et al. .............. 607/5 |
| 2004/0015041 | A1 | * | 1/2004 | Melvin ........................ 600/16 |
| 2004/0162463 | A1 | * | 8/2004 | Lau et al. ..................... 600/37 |
| 2005/0160823 | A1 | * | 7/2005 | Zdeblick et al. .............. 73/715 |

* cited by examiner

*Primary Examiner* — Nicole F Lavert
(74) *Attorney, Agent, or Firm* — Pillsbury Winthrop Shaw Pittman LLP

(57) ABSTRACT

An electromagnetic cardiac assembly adapted to assist ventricular output in a human heart includes a magnetic mat adapted for mounting inside a human body near the heart. The mat is made from a material responsive to application of an electromagnetic field so as to be movable into compressive relation with the heart in response to application of the electromagnetic field thereto and movable out of said compressive relation to permit the heart to relax when application of the electromagnetic field is discontinued. The assembly also includes an electromagnetic subassembly adapted for mounting on the human body in functionally cooperative relation with respect to the mat, and an energy dispersion device adapted for mounting between the mat and the heart. The energy dispersion device is constructed and arranged to disperse energy between the mat and the heart.

23 Claims, 3 Drawing Sheets

CARDIAC TISSUE ENERGY DISPERSION DEVICE

CROSS-REFERENCE TO RELATED APPLICATIONS

This application claims the benefit of priority from U.S. Provisional Patent Application Ser. Nos. 60/755,413, 60/755,414, 60/755,415, 60/755,416, and 60/755,424, all of which were filed Dec. 31, 2005, the contents of which are incorporated herein by reference in their entireties. The present application is related to U.S. patent application Ser. Nos. 11/648,635, 11/648,636, 11/648,637, and 11/648,908, all of which were filed on Jan. 3, 2007, and are incorporated herein by reference in their entireties.

BACKGROUND OF THE INVENTION

1. Field of the Invention

This invention generally relates to an energy dispersion device for tissues, and more particularly to an electromagnetic cardiac assist device having an energy dispersion device, and a method for assisting ventricular output in the human heart.

2. Description of Related Art

During the aging process, weakened or ineffective cardiac muscles may inhibit the cardiac pumping function from either the right, left, or both ventricles. When the pumping activity of the heart cannot meet the body's demands, systemic shock and subsequent organ dysfunction (such as pulmonary edema and renal failure) can result. Weakened heart muscles can also result in an over-distended, dilated myocardium, which may have a detrimental effect on the electrical conduction and overall mechanical performance of the heart.

Advances in medical science have attempted to overcome these problems by replacing an impaired heart via heart transplants, or with devices such as artificial hearts. However, heart transplants are difficult to obtain since there is a limited donor supply. Moreover, artificial hearts have proved not entirely effective in duplicating cardiac contractions, are extremely expensive, and are known to be rejected by the human body. Therefore, rather than replacing the heart, various arrangements have been proposed to assist right and left ventricular output of the existing impaired heart.

For example, a number of arrangements are suggested in U.S. Pat. No. 4,621,617 to Sharma ("the '617 patent). FIG. 1 of the '617 patent proposes an arrangement in which two components are disposed in surrounding relation to the heart and function to compress the heart therebetween to assist ventricular output thereof. The two components are furnished with electromagnetic induction circuitry, numerous pole elements, and are secured to one another by a mechanical hinge. It can be appreciated that the device is quite cumbersome, difficult to implant, and has achieved little, if any, acceptance. FIG. 4 of the '617 patent illustrates an alternate arrangement in which a compressor element is provided posteriorly to the heart and is movable to compress the heart against the rib cage. This embodiment is somewhat more practical, but nevertheless problematic in a number of respects. For example, no means are provided for evaluating the amount of compressive resistance or intra-cardiac pressure of the heart during compression thereof. As a result, the compressor element may either apply insufficient compressive force to the heart, thereby resulting in ineffective ventricular assist, or apply excessive compressive force, thereby damaging the heart. Additionally, providing a compressor element posteriorly to the heart requires complex surgery in which the entire chest cavity must be opened. Moreover, such placement of the compressor element is largely impractical since the aorta, esophagus and spine are all disposed in close proximity to the posterior portion of the heart, and leave little room for insertion of any type of assist device.

U.S. Pat. No. 5,498,228 ("the '228 patent"), which is incorporated herein by reference in its entirety, discloses an electromagnetic bi-ventricular device that includes a magnetic mat that is moved towards the vertebral body to compress the heart therebetween in response to the application of an electromagnetic field directed thereto. Although the device includes a transducer and control circuit to regulate the compressive force that is applied to the heart, direct cardiac compression, while attempting to augment cardiac output in the failing heart, may result in trauma to the epicardium and potentially to the myocardium.

It is desirable to improve the electromagnetic biventricular assist device that is disclosed in the '228 patent so that tissue injury may be minimized.

BRIEF SUMMARY OF THE INVENTION

It is an aspect of the present invention to provide an electromagnetic biventricular assist device to augment cardiac output in a safe manner, without injury to the heart or surrounding tissues.

In an embodiment of the invention, an electromagnetic cardiac assembly adapted to assist ventricular output in a human heart is provided. The electromagnetic cardiac assembly includes a magnetic mat adapted for mounting inside a human body near the heart. The mat is made from a material responsive to application of an electromagnetic field so as to be movable in a first direction into compressive relation with the heart in response to application of the electromagnetic field thereto and movable in a second direction out of the compressive relation to permit the heart to relax when application of the electromagnetic field is discontinued. The electromagnetic cardiac assembly also includes an electromagnetic subassembly adapted for mounting on the human body in functionally cooperative relation with respect to the mat, and for alternately generating and discontinuing the electromagnetic field so that the mat alternately moves into and out of the compressive relation with the heart. The electromagnetic cardiac assembly also includes an energy dispersion device adapted for mounting between the mat and the heart. The energy dispersion device is constructed and arranged to disperse energy between the mat and the heart. The electromagnetic cardiac assembly further includes a transducer for evaluating compressive resistance of the heart during movement of the mat into compressive relation with the heart and for generating an electrical signal as a function of the compressive resistance of the heart. A control circuit is constructed and arranged to receive the signal generated by the transducer and to control an intensity level of the electromagnetic field generated by the electromagnetic subassembly as a function of the signal to thereby control a degree to which the mat compresses the heart.

In an embodiment of the invention, an electromagnetic cardiac assembly for assisting ventricular output in a human heart is provided. The electromagnetic cardiac assembly includes a magnetic mat adapted for mounting inside a human body near the heart. The mat includes a material responsive to application of an electromagnetic field so as to be movable in a first direction into compressive relation with the heart in response to application of the electromagnetic field and movable in a second direction out of the compressive relation to permit the heart to relax when application of the electromagnetic field is discontinued. The electromagnetic cardiac assembly also includes an electromagnetic subassembly adapted for mounting on the human body in functionally cooperative relation with respect to the mat, and for alternately generating and discontinuing the electromagnetic field so that the mat alternately moves into and out of the compressive relation with the heart. The electromagnetic cardiac assembly also includes an energy dispersion device adapted for mounting between the mat and the heart. The energy dispersion device is constructed and arranged to disperse energy between the magnetic mat and the heart. The electromagnetic cardiac assembly further includes a pressure transducer for measuring intra-cardiac pressure within the heart and for generating a signal as a function of the intra-cardiac pressure, and a control circuit for receiving the signal generated by the transducer and for controlling an intensity of the electromagnetic field generated by the electromagnetic subassembly as a function of the signal to thereby control a degree to which the mat compresses the heart as a function of the intra-cardiac pressure within the heart.

In an embodiment of the invention, a method for assisting ventricular output in a human heart by compressing the heart against a vertebral body is provided. The method includes detecting an electrocardiogram as a function of electrical activity of the heart, generating an electromagnetic field with an electromagnetic assembly as a function of the electrocardiogram, moving a magnetic mat disposed anteriorly to the heart towards the vertebral body so as to force the heart against the vertebral body and thereby compress the heart between the magnetic mat and the vertebral body in response to application of the electromagnetic field to the mat, and dispersing energy provided by the magnetic mat with an energy dispersion device between the magnetic mat and the heart when the heart is forced against the vertebral body.

These and other aspects and advantages of the invention will be apparent from the following description, the accompanying drawings, and the appended claims.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE INVENTION

Figure 1:
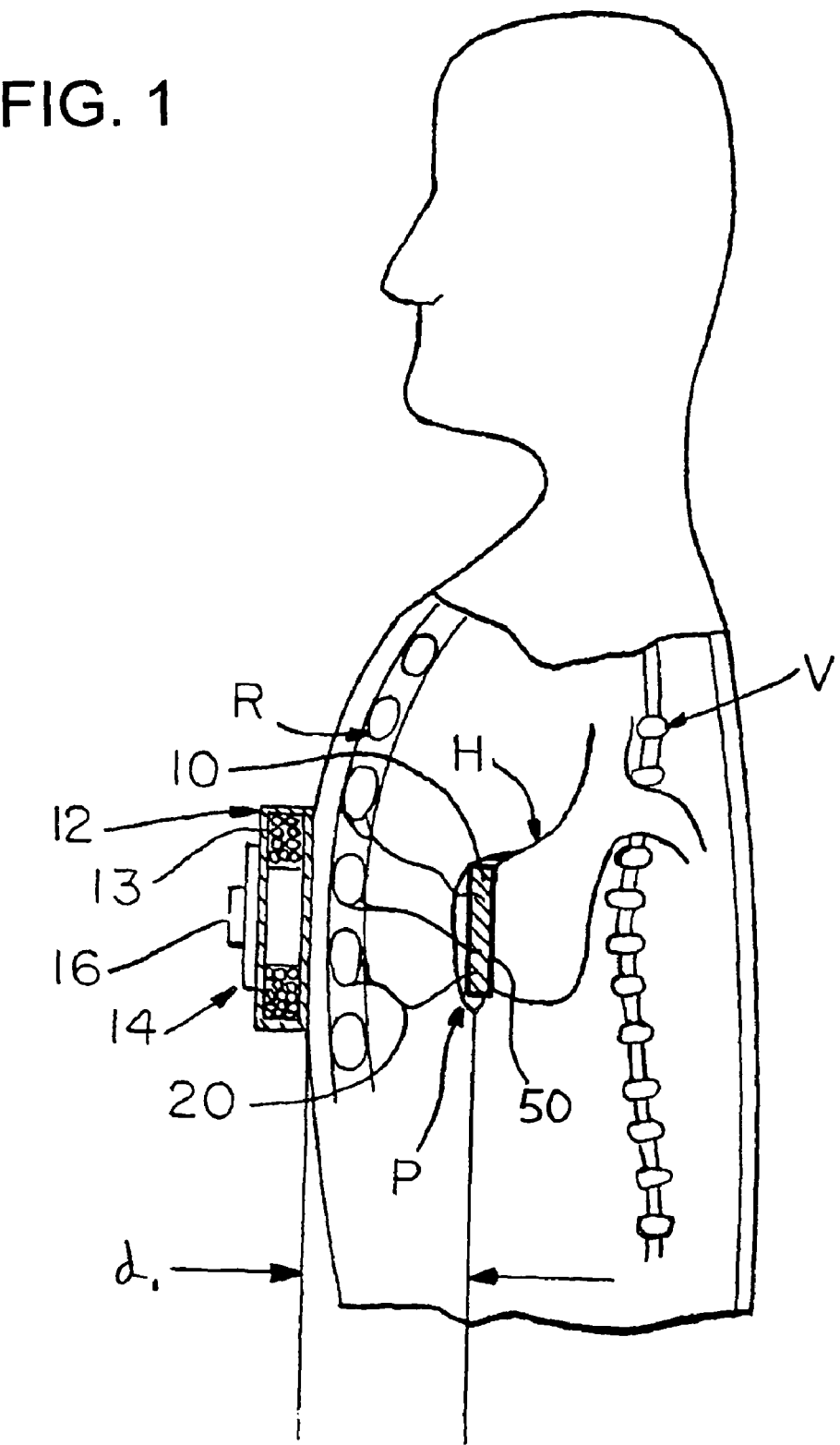
FIG. 1 is a side sectional view of the cardiac assist device of an embodiment of the present invention shown inside the human body in non-compressive relation with the heart.

FIG. 1 is a side sectional view taken through the human body and the cardiac assist device of the present invention, which is shown in non-compressive relation with the human heart.

In the illustrated embodiment, the device includes a magnetic mat 10 which is adapted to be mounted inside the human body inside of the rib cage R, near the heart H. Preferably, the mat 10 is a permanent magnet made from a flexible ferromagnetic material, including but not limited to samarium cobalt, neodymium iron, and neodymium iron boron (NeFeBo). It can be appreciated, however, that the mat 10 may comprise other materials (such as a superconductive material) so long as the mat 10 is sufficiently responsive to application of an electromagnetic field to compress the heart in accordance with the principles of the present invention. Regardless of the material used, however, the exterior surface of the mat should be chemically inert, and not immunogenic, so that it does not react with blood, tissue, or organs. If necessary, the mat may be coated or surrounded by an inert substance, including but not limited to polyvinyl chloride (PVC), polytetraflouroethylene (PTFE), and zinc.

A general principal in tissue energy dispersion is that the smaller the focus of energy/force to the tissue, the greater the tissue trauma; conversely, the larger the focus of energy/force to the tissue, the smaller the tissue trauma. For example, five pounds of force exerted on muscle will cause less tissue damage if it is spread out and evenly distributed over the entire surface of the muscle, as compared to five pounds of force focused on only a 1 $cm^2$ area of the muscle. The mechanical energy delivered into living tissue can be represented by the change of force divided by the change in time, i.e., $\Delta F/\Delta t$. In a plot of force applied to the tissue as a function of time, the energy that is delivered to tissue, $\Delta F/\Delta t$, is the average slope of the plot. The steeper the slope, the shorter the period of time for energy transfer to take place, and the greater the likelihood of tissue trauma. Similarly, the less steep the slope, the less likely tissue injury will be realized, because the period of time for energy transfer to take place is longer.

In order to lessen any potential tissue trauma that may result if the hard surface of the mat 10 is brought into direct contact with the epicardium of the heart, an energy dispersion device 50 may be positioned between the mat 10 and the heart H, as shown in FIG. 1, such that the energy dispersion device 50 is located adjacent to the heart H. The energy dispersion device 50 is constructed and arranged to provide a more gradual and evenly distributed energy transfer between the mat 10 and the heart H. The energy dispersion device 50 is preferably made from a soft material, such as silicone, or a silicone-like substance. The soft material may be gel-like, and may take the form of a sleeve in which the mat 10 may be inserted, or may be provided, for example, as a sheet of material in between the mat 10 and the anterior aspect of the heart H. In an embodiment, the mat may be completely surrounded by the soft material such that the mat is embedded and sealed within in the energy dispersion device.

Figure 3:
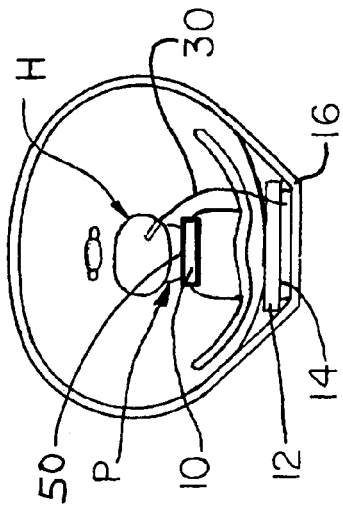
FIG. 3 is a top sectional view showing the cardiac assist device of an embodiment of the present invention inside the human body.

The mat 10 and the energy dispersion device 50 are supported within the body, preferably in the space between the anterior aspect of the heart H and the posterior aspect of the pericardium P, as shown in FIG. 1, although, as will be described later, the mat 10 can also be positioned anteriorly to both the heart H and pericardium P, as shown in FIG. 3. Preferably, the mat/energy dispersion device support comprises a plurality of heavy mono-filament threads 20 each having one end secured to the mat 10 and/or energy dispersion device 50, and another end secured to the rib cage R (or sternum). The threads are flexible to permit movement of the mat 10 and the energy dispersion device 50, and should be sufficiently strong to withstand continued flexing without breakage. Where the mat 10 and the energy dispersion device 50 are disposed between the heart H and pericardium P, the threads 20 may be sutured through the pericardium P. It can be appreciated that many alternatives to the mono-filament threads can be used to support the mat and energy dispersion device, as long as such alternatives maintain the mat and the energy dispersion device in movably supported relation, anteriorly and proximate to the heart.

Figure 2:
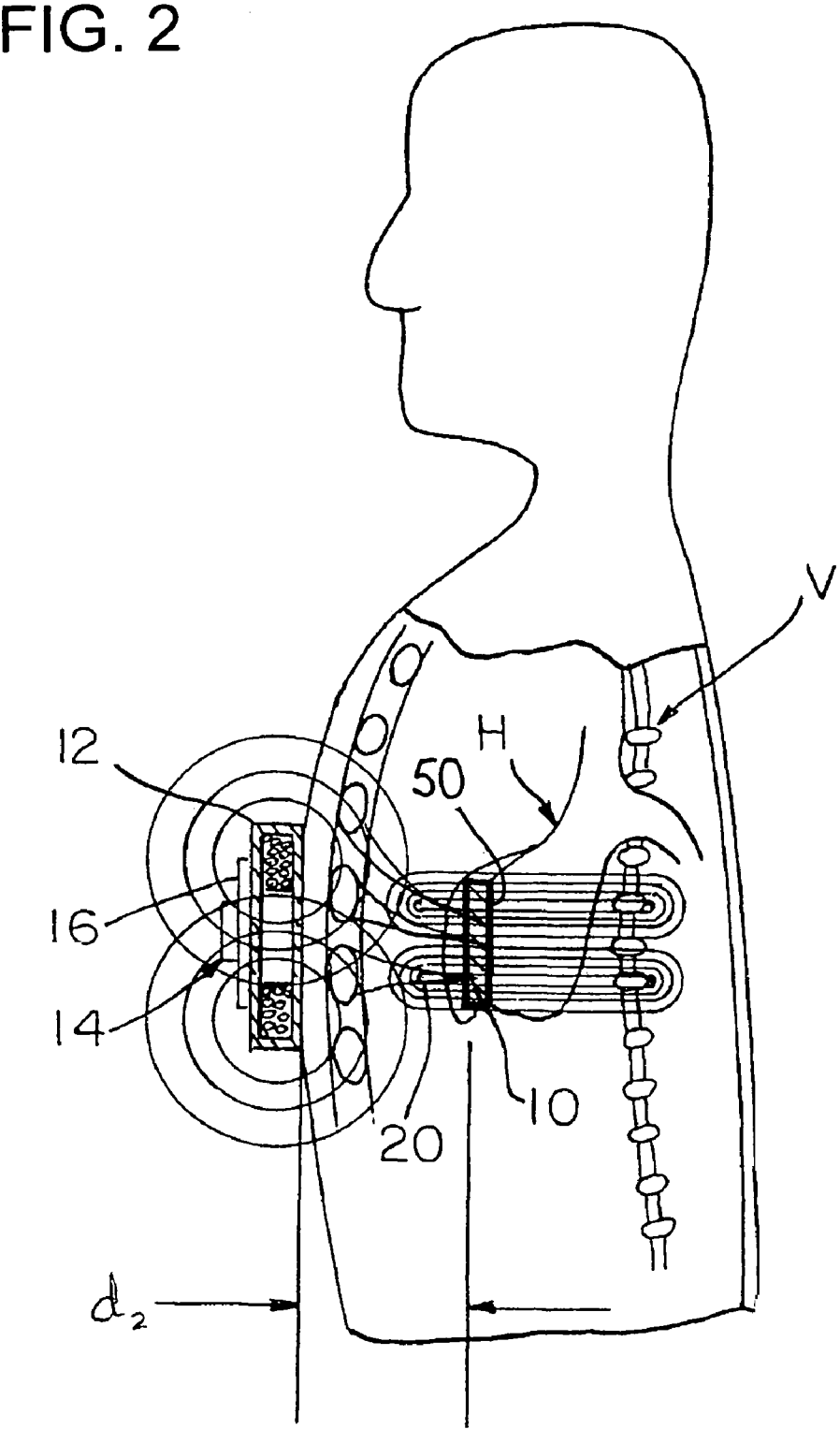
FIG. 2 is a side sectional view of the cardiac assist device of FIG. 1 shown inside the human body in compressive relation with the heart.

An electromagnetic assembly 12 is adapted to be mounted externally on the human body, preferably on the chest, in functionally cooperative relation with respect to the mat 10, at a distance represented by $d_1$ in FIG. 1. The electromagnetic assembly 12 includes an inductive coil 13 to which a current is supplied (preferably by a D.C. battery, not shown) to produce an electromagnetic field in a first direction, which repels the mat 10 into compressive relation with the heart H, as shown in FIG. 2, which causes the distance between the mat 10 and the electromagnetic assembly 12 to increase to $d_2$. More particularly, electromagnetic assembly 12 alternately generates and discontinues the electromagnetic field to alternately compress the heart against vertebral body V (e.g., the spine) and then permit the heart to relax, thereby assisting the mechanical pumping function of the heart. The magnitude of the force produced will be proportionally dependent on the mat's magnetic field strength, the amount of current traveling through the electromagnetic assembly 12, and the number of current-turns in the electromagnetic assembly 12, but inversely proportional to the distance between the electromagnetic assembly and the mat.

In an embodiment, the electromagnetic assembly 12 may be further arranged to produce an electromagnetic field in a second direction that is opposite the first direction described above. Specifically, the current that is supplied to the coil 13 to generate the electromagnetic field may be reversed, which will cause the electromagnetic field to be reversed, thereby attracting the magnetic mat 10 rather than repelling the mat 10. Further details of such an arrangement are provided in U.S. Provisional Patent Application No. 60/755,416, which is incorporated herein by reference, and U.S. patent application Ser. No. 11/648,636, which is incorporated herein by reference.

A transducer 14 (preferably a load cell, force gauge type, made from piezo AC material) is secured to the electromagnetic assembly 12 on the side opposite the chest by a preferably rigid harness 16. The harness is disposed in surrounding relation to the human torso as shown in FIG. 3, which is a top sectional view through the torso. The harness 16 may include shoulder straps to prevent vertical movement of the electromagnetic assembly 12 when an individual is in the upright position.

In FIG. 3, the mat 10 and energy dispersion device 50 are shown to be positioned anteriorly to both the heart H and pericardium P. It can be appreciated, however, that it is more preferable to position the mat 10 in the natural space between the heart H and pericardium P to enable the mat 10 to more effectively compress the heart by being closer to the heart H, i.e., being almost in direct contact with the heart H, with the energy dispersion device 50 being disposed therebetween. In such an embodiment, the energy dispersion device 50 preferably substantially surrounds the mat 10 so as to protect the heart and the pericardium from the hard surface of the mat. It is noted that placement of the mat 10 and energy dispersion device 50 anteriorly to the pericardium P may be more difficult since a significant amount of body tissue between the pericardium P and sternum may need to be removed to enable such placement.

Figure 4:
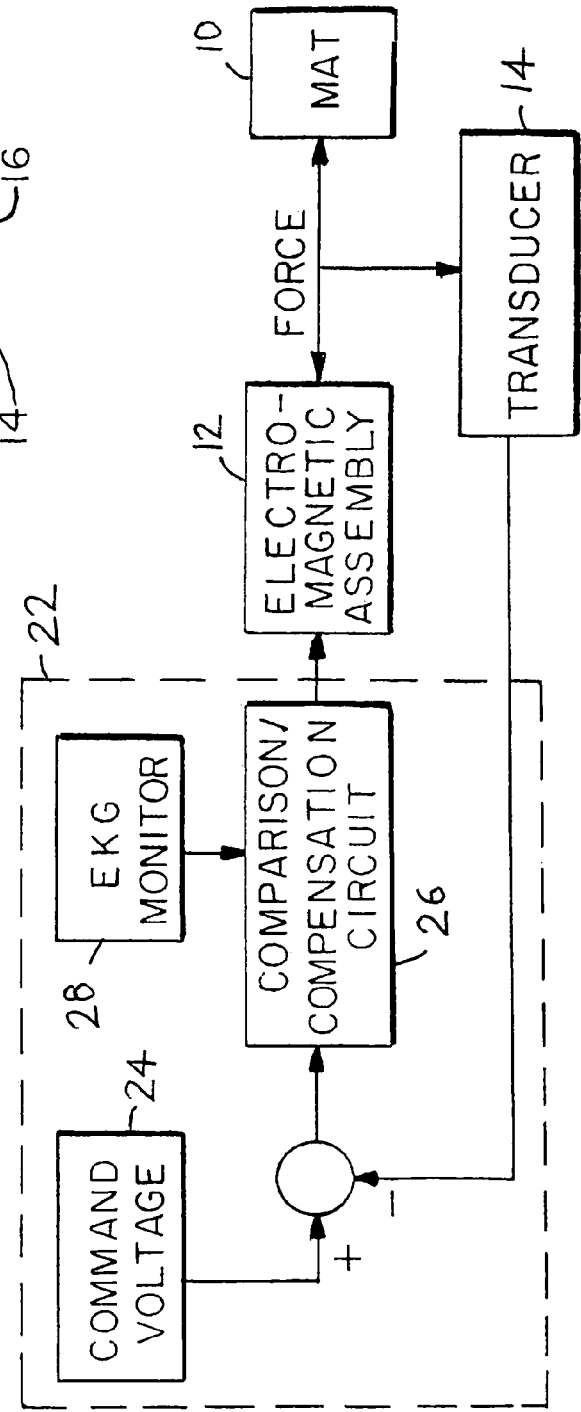
FIG. 4 is a block diagram schematically showing the interrelation of various components of the cardiac assist device of FIG. 1.

As shown in FIG. 4, the transducer 14 forms part of an electronic feedback/control loop, and functions to evaluate the compressive resistance of the heart during movement of the mat into compressive relation with the heart. More specifically, when the electromagnetic assembly 12 generates an electromagnetic field to repel mat 10, an equal and opposite force is applied to the electromagnetic assembly, thus repelling the assembly away from the chest. It can be appreciated that when such an electromagnetic field is generated, pressure transducer 14 is compressed between the assembly 12 and harness 16 (e.g., see FIG. 2). The transducer 14 senses the compressive pressure or force applied thereto and outputs a voltage proportional to such force or pressure. A control circuit 22 receives the signal generated by the transducer and controls the intensity of the electromagnetic field generated by the electromagnetic assembly as a function of that signal. As a result, the control circuit effectively controls the degree to which the mat compresses the heart.

More specifically, control circuit 22 includes a compensation/comparison circuit 26 (or "compensation circuit") which compares the voltage generated by transducer 14 to a command voltage generated by command voltage generator 24. The command voltage corresponds to a predetermined voltage which represents the ideal amount of force required to compress the heart. The compensation/comparison circuit 26 measures the difference between the voltage generated by the pressure transducer 14 and the command voltage, and then digitally compensates for such difference so that an appropriate amount of current is sent through the coil 13 in the electromagnetic assembly 12. For example, if the voltage generated by transducer 14 is less than the command voltage, the compensation circuit 26 will ramp up the current sent through the coil 13 and thereby increase the intensity of the magnetic field applied by electromagnetic assembly 12. In contrast, if the voltage generated by transducer 14 is less than the command voltage, the compensation circuit will decrease the amount of current through the coil 13 and thereby decrease the intensity of the magnetic field applied by the electromagnetic assembly 12. Thus, the intensity or magnitude of the electromagnetic field generated by the electromagnetic assembly is controlled so that the compressive force applied by the mat 10 to the heart remains within a predetermined range with each compressive stroke. The presence of the energy dispersion device 50 helps to ensure that the energy provided to the heart H from the mat 10 is more gradually transferred and more evenly distributed to the heart H than if the energy dispersion device was not present.

The predetermined amount of force to be applied to the heart in order to obtain the desired cardiac output is determined experimentally during an initial procedure wherein a catheter, such as the Swan-Ganz catheter, is placed in the heart to monitor intra-ventricular pressures. This type of catheter is also capable of measuring actual cardiac output. The cardiac output and intra-cardiac pressure are correlated with the voltages generated by pressure transducer 14, and after several days of experimentation, the Swan-Ganz catheter may be removed. The pressure transducer 14 thereafter generates a voltage as a function of the compressive resistance of the heart, which in turn is a function of either the intra-cardiac pressure or output of the heart.

It can be appreciated that the Swan-Ganz catheter may be kept within the heart and utilized as a transducer in lieu of transducer 14. Such an arrangement is shown in FIG. 3, wherein a Swan-Ganz catheter 30 is in place. It is advantageous, however, to remove the Swan-Ganz catheter since use thereof requires the provision of wires extending through the human flesh from the catheter to the electromagnetic assembly 12 and control circuit, which may be quite uncomfortable for the subject.

While the magnitude of the electromagnetic field generated by electromagnetic assembly 12 is controlled by the control circuit 22 together with the pressure transducer 14, it can be appreciated that the frequency of the electromagnetic field must coincide with the natural contractions of the heart.

This may be accomplished by use of an electrocardiogram (EKG) 28 monitor integrated into the control circuit. The EKG monitor measures the electrical activity of the heart and, together with the rest of the control circuit, functions to synchronize the electromagnetic field generated by the electromagnetic assembly with the QRS spike of the electrocardiogram. This technique of adjusting the rate at which the mat compresses the heart is similar to that used in intra-aortic balloon pumps, and is conventional in this field of technology. Other devices may be used to monitor the electrical activity of the heart. The use of an EKG monitor is provided as an example, and should not be considered to be limiting in any way.

The preferred procedure for inserting the mat 10 and the energy dispersion device 50 into the human body in cooperative relation the heart will now be described. The mat 10 is placed inside the energy dispersion device 50 when the energy dispersion device 50 is provided as a sleeve, or is placed in contact with the one side of the energy dispersion device 50 when the energy dispersion device 50 is provided as a sheet of material, and then the mat and energy dispersion device may be inserted into the body at the same time. When the energy dispersion device 50 is provided as a sheet of material, the energy dispersion device may be inserted into the body before the mat is inserted into the body. The heavy mono-filament threads 20 each have one end thereof secured to the peripheral edges of two opposite sides of the mat and energy dispersion device, which preferably have a substantially rectangular or oval shape. An incision is made immediately below the breastbone using the sub-xiphoid approach, and the threads are then sutured to the rib cage and/or sternum by use of curved trochar sheath. The sutures are passed anteriorly to the epicardium, but posterior to the anterior aspect of the pericardium, and exit intercostally lateral to the sternum. Enough slack should be left in the mono-filament sutures to permit movement of the mat 10 and energy dispersion device 50 away from the electromagnetic assembly 12 into compressive relation with the heart upon application of the electromagnetic field.

While the assembly of the present invention can be used to temporarily assist the mechanical pumping function of the heart (for example, in patients waiting for cardiac transplants, patients with septic shock whose heart is disabled until the endotoxin and/or cardiodepressant factor has been cleared, and patients in cardiogenic shock due to acute ischemia), the invention can also be used as permanent cardiac assist device as it is intended to function for a great number of years with little or no maintenance. The inclusion of the energy dispersion device may prolong the usefulness of the device for those patients needing long-term care, as the potential injury to the tissues of the heart the tissues that surround the heart may be minimized.

The assembly in accordance with the principles of the present invention has additional benefits in that it alleviates problems associated with an over-distended, dilated myocardium as the repeated application of compressive force on the heart tends to decrease the heart size (or at least inhibit growth thereof). This is beneficial to electrical conduction and thus mechanical performance of the heart.

Although the energy dispersion device of the present invention is discussed above for use in a cardiac assist device for the heart, it is contemplated that the energy dispersion device may have broader utility in a wide variety of applications. For example, it is contemplated that the mat and energy dispersion device described above may be configured to be used with tissues and muscles other than the heart, or may even be used as an artificial muscle. The above-described and illustrated embodiments are not intended to be limiting in any way.

While specific embodiments of the invention have been described above, it will be appreciated that the invention may be practiced otherwise than as described. The descriptions above are intended to be illustrative, not limiting. Thus, it will be apparent to one skilled in the art that modifications may be made to the invention as described without departing from the scope of the claims set out below.

What is claimed is:

1. An electromagnetic cardiac assembly adapted to assist ventricular output in a human heart, the electromagnetic cardiac assembly comprising:

a magnetic mat adapted for mounting inside a human body near the heart, said mat being made from a material responsive to application of an electromagnetic field so as to be movable in a first direction into compressive relation with the heart in response to application of the electromagnetic field thereto and movable in a second direction out of said compressive relation to permit the heart to relax when application of said electromagnetic field is discontinued;

an electromagnetic subassembly adapted for mounting on the human body in functionally cooperative relation with respect to said mat, and for alternately generating and discontinuing said electromagnetic field so that said mat alternately moves into and out of said compressive relation with the heart;

an energy dispersion device made from a soft material, the energy dispersion device adapted for mounting between said mat and the heart so that the mat does not contact the heart, said energy dispersion device being constructed and arranged to disperse energy between said mat and the heart when the mat is moved into compressive relation with the heart so that the energy is gradually transferred and evenly distributed to the heart;

a transducer for evaluating compressive resistance of the heart during movement of said mat into compressive relation with the heart and for generating an electrical signal as a function of said compressive resistance of the heart; and a control circuit constructed and arranged to receive said signal generated by said transducer and to control an intensity level of the electromagnetic field generated by said electromagnetic subassembly as a function of said signal to thereby control a degree to which said mat compresses the heart.

2. The electromagnetic cardiac assembly according to claim 1, further comprising a flexible support adapted to secure the mat and the energy dispersion device to a human rib cage in movable relation between the heart and the rib cage.

3. The electromagnetic cardiac assembly according to claim 2, wherein said flexible support comprises heavy mono-filament threads, and wherein said mat is adapted to be disposed between an anterior aspect of the heart and a posterior aspect of the pericardium, said threads extending from the mat through the pericardium to the rib cage.

4. The electromagnetic cardiac assembly according to claim 1, wherein said magnetic mat and said energy dispersion device are substantially flexible so as to be adapted to conform to the shape of the heart.

5. The electromagnetic cardiac assembly according to claim 4, wherein said magnetic mat and comprises a permanent magnet surrounded by an insulative layer, and wherein said electromagnetic field generated by said electromagnetic subassembly magnetically repels the mat away therefrom into said compressive relation with the heart.

6. The electromagnetic cardiac assembly according to claim 4, wherein said magnetic mat comprises neodymium iron boron, and said insulative layer comprises zinc.

7. The electromagnetic cardiac assembly according to claim 1, wherein said soft material comprises silicone.

8. The electromagnetic cardiac assembly according to claim 1, wherein said energy dispersion device comprises a sleeve that substantially surrounds said magnetic mat.

9. The electromagnetic cardiac assembly according to claim 1, wherein said energy dispersion device comprises a sheet of the soft material.

10. The electromagnetic cardiac assembly according to claim 1, further comprising a harness for mounting said electromagnetic subassembly on the human body.

11. The electromagnetic cardiac assembly according to claim 1, wherein said electromagnetic subassembly comprises an inductive coil, and wherein said control circuit controls an amount of current which travels through said coil, the amount of current which travels through said coil being proportional to an intensity level of the electromagnetic field generated by said electromagnetic subassembly.

12. The electromagnetic cardiac assembly according to claim 1, wherein said electromagnetic subassembly is constructed and arranged to reverse said electromagnetic field after said electromagnetic field has been discontinued, and wherein said magnetic mat is responsive to application of the reversed electromagnetic field so as to be movable in the second direction.

13. An electromagnetic cardiac assembly for assisting ventricular output in a human heart comprising:

a magnetic mat adapted for mounting inside a human body near the heart, said mat comprising a material responsive to application of an electromagnetic field so as to be movable into compressive relation with the heart in response to application of the electromagnetic field and movable out of said compressive relation to permit the heart to relax when application of said electromagnetic field is discontinued;

an electromagnetic subassembly adapted for mounting on the human body in functionally cooperative relation with respect to said mat, and for alternately generating and discontinuing said electromagnetic field so that said mat alternately moves into and out of said compressive relation with the heart;

an energy dispersion device made from a soft material, the energy dispersion device adapted for mounting between said mat and the heart so that the mat does not contact the heart, said energy dispersion device being constructed and arranged to provide a gradual and evenly distributed energy transfer between said mat and the heart when the mat is moved into compressive relation with the heart;

a pressure transducer for measuring intra-cardiac pressure within the heart and for generating a signal as a function of said intra-cardiac pressure; and a control circuit for receiving said signal generated by said transducer and for controlling an intensity of said electromagnetic field generated by said electromagnetic subassembly as a function of said signal to thereby control a degree to which the mat compresses the heart as a function of the intra-cardiac pressure within the heart.

14. The electromagnetic cardiac assembly according to claim 13, further comprising a flexible support adapted to secure the mat and the energy dispersion device to a human rib cage in movable relation between the heart and the rib cage.

15. The electromagnetic cardiac assembly according to claim 14, wherein said flexible support comprises heavy mono-filament threads, and wherein said mat and said energy dispersion device are adapted to be disposed between an anterior aspect of the heart and a posterior aspect of the pericardium, said threads extending from the mat and/or the energy dispersion device through the pericardium to the rib cage.

16. The electromagnetic cardiac assembly according to claim 13, wherein said magnetic mat comprises a permanent magnet, and wherein said electromagnetic field generated by said electromagnetic subassembly magnetically repels the mat away therefrom into said compressive relation with the heart.

17. The electromagnetic cardiac assembly according to claim 16, wherein said magnetic mat comprises neodymium iron boron.

18. The electromagnetic cardiac assembly according to claim 13, wherein said soft material comprises silicone.

19. The electromagnetic cardiac assembly according to claim 13, wherein said energy dispersion device comprises a sleeve that substantially surrounds said magnetic mat.

20. The electromagnetic cardiac assembly according to claim 13, wherein said energy dispersion device comprises a sheet of the soft material.

21. The electromagnetic cardiac assembly according to claim 13, wherein said pressure transducer comprises a Swan-Ganz catheter.

22. The electromagnetic cardiac assembly according to claim 13, wherein said electromagnetic subassembly comprises an inductive coil, and wherein said control circuit controls an amount of current which travels through said coil, the amount of current which travels through said coil being proportional to the intensity level of the electromagnetic field generated by said electromagnetic subassembly.

23. The electromagnetic cardiac assembly according to claim 13, wherein said electromagnetic subassembly is constructed and arranged to reverse said electromagnetic field after said electromagnetic field has been discontinued, and wherein said magnetic mat is responsive to application of the reversed electromagnetic field so as to be movable in the second direction.

\* \* \* \* \*